United States Patent [19]

Miller et al.

[11] 4,068,379
[45] Jan. 17, 1978

[54] ORTHODONTIC APPLIANCE WITH POROUS TOOTH-ABUTTING FACE

[75] Inventors: Frank R. Miller, Azusa; Craig A. Andreiko, Pasadena; Kenneth W. Premo, Fullerton, all of Calif.

[73] Assignee: Ormco Corporation, Glendora, Calif.

[21] Appl. No.: 802,011

[22] Filed: June 1, 1977

Related U.S. Application Data

[63] Continuation-in-part of Ser. No. 779,056, March 18, 1977, abandoned, which is a continuation-in-part of Ser. No. 677,412, April 15, 1976, abandoned.

[51] Int. Cl.² ............................................. A61C 7/00
[52] U.S. Cl. ................................................... 32/14 A
[58] Field of Search .................... 29/160.6; 245/10, 2; 140/107; 139/425 R; 228/178

[56] References Cited

U.S. PATENT DOCUMENTS

| | | |
|---|---|---|
| 1,078,380 | 11/1913 | Reynolds .............................. 245/2 |
| 2,082,513 | 6/1937 | Roberts ................................ 245/2 |
| 2,374,422 | 4/1945 | Dahl ................................... 32/10 A |
| 3,926,358 | 12/1975 | Hester ............................... 228/173 A |

OTHER PUBLICATIONS

"TP Straight Talk" vol. 5, Nos. 2 and 3, May–June 1974, "Special Report on Direct Bonding," TP Labs, Inc., P.O. Box 73, Laporte Indiana, 46350 U.S.A.

*Primary Examiner*—Robert Peshock

[57] ABSTRACT

Attachment of an orthodontic appliance by direct bonding to a tooth utilizing a composite base with a porous tooth-abutting face and various methods for making the device, such as casting as a unitary structure, or forming the composite base by rolling a mesh, in strip form, so as to form flats on at least one surface of the mesh where the mesh is to be in contact with a solid base portion, then bonding the mesh to the base. In the latter embodiment, the metal base is a metal foil to which the appliance is attached and the mesh and foil form a composite strip, from which individual composite pads are formed.

16 Claims, 20 Drawing Figures

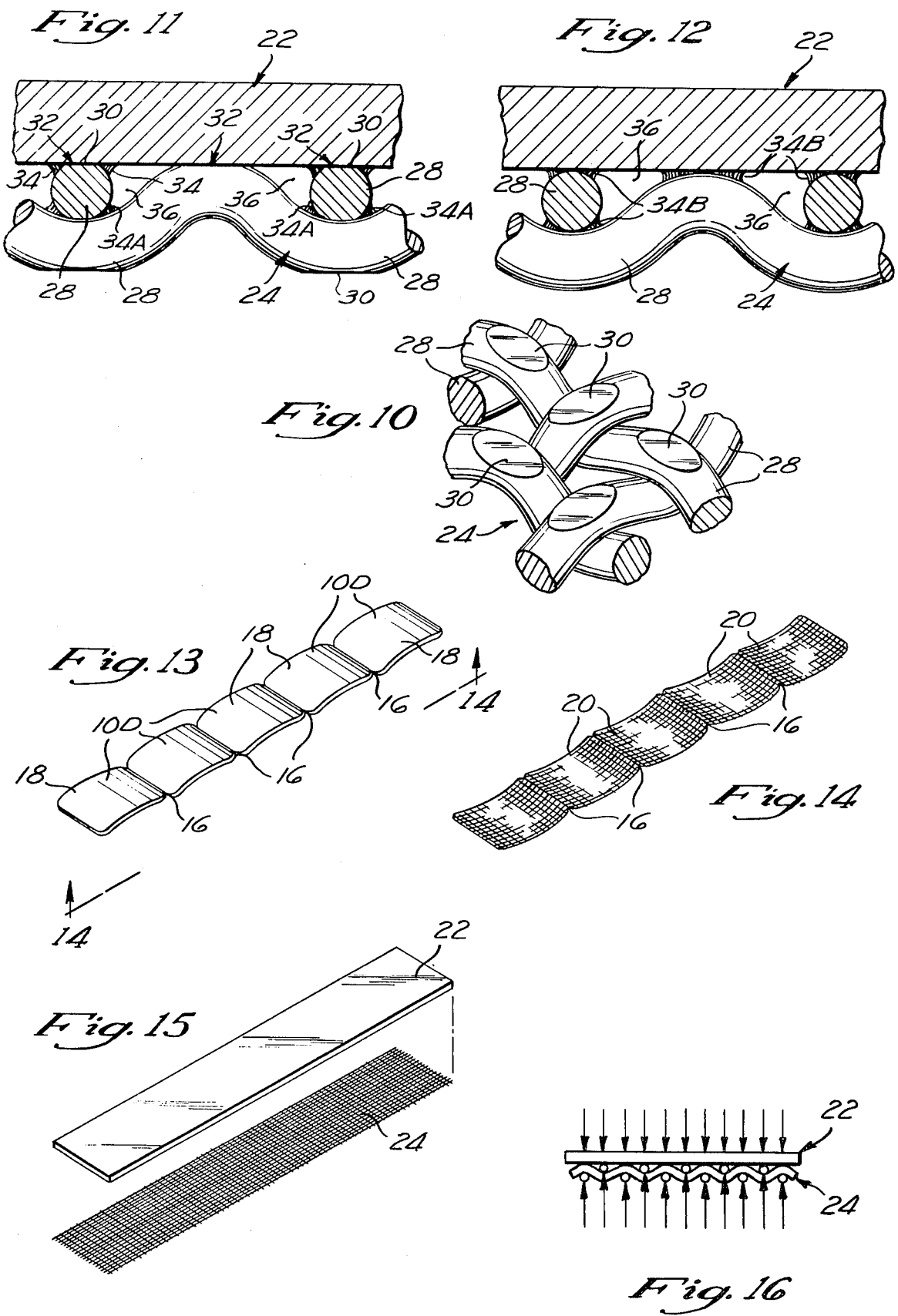

ORTHODONTIC APPLIANCE WITH POROUS TOOTH-ABUTTING FACE

CROSS REFERENCE TO RELATED APPLICATION

This application is a continuation-in-part of pending U.S. patent application Ser. No. 779,056, filed Mar. 18, 1977, and now abandoned, which application is a continuation-in-part of U.S. Pat. application Ser. No. 677,412, filed Apr. 15, 1976, now abandoned.

BACKGROUND OF THE INVENTION

1. Field of the Invention

This invention relates to devices for the attachment of an orthodontic appliance to a tooth and methods for making such a device.

2. Description of the Prior Art

The well-known practice of using bands to secure orthodontic appliances to the teeth is not generally desirable because bands create spaces between the teeth which must be closed at the conclusion of the orthodontic treatment. A bracket made of plastic and bonded directly to the tooth has been utilized for attachment of an orthodontic appliance directly to the tooth, thereby eliminating the band, as is shown in U.S. Pat. No. 3,303,565. Even though a plastic bracket bonds well to a tooth, such brackets have not generally provided the structural strength and control required for many types of orthodontic treatment. Thus, metal brackets fixed to composite metal and flexible plastic bases have been used in attempting to provide greater rigidity, as shown, for example, in U.S. Pat. No. 3,250,003.

A series of openings through a base pad, either metal, U.S. Pat. No. 3,932,940, or plastic, U.S. Pat. No. 3,765,091, on to which an orthodontic appliance is mounted, have been utilized with a suitable cement to help retain and bond the pad to the tooth. The holes allow the cement to flow into the openings to provide additional mechanical strength to the bond between the pad and the tooth. However, such plastic bases suffer from a lack of rigidity although providing good bonding, while such metal bases suffer from weak bonding while providing good rigidity. In both instances, the cement flows through the holes into the orthodontic appliance when being bonded to the tooth. The cement can not be immediately removed, because attempting to do so would move the device while the cement is curing, thereby negating the precise positioning required for orthodontic treatment. However, if the orthodontist waits to remove the excess cement from the appliance until the pad is reasonably securely bonded to the tooth, the cement has already bonded itself to the appliance, and therefore is difficult to remove.

Another base of this type is a pad of metal screen or mesh, to which the orthodontic appliance is attached by spot welding. Such devices, currently sold by American Orthodontics, Sheboygan, Wis., suffer from a weak attachment of the appliance to the pad, as well as not providing the strength of bonding of a plastic base or the rigidity of a metal base, and permitting an even greater amount of cement to pass through the base pad and contact the appliance. In a modified type of such a device, also sold by American Orthodontics, the appliance is mounted on a metallic base pad, which may be either plain or perforated, to which a pad of metal screen or mesh is attached by spot welding, so as to fix the screen to the base pad on the side of the pad opposite the appliance. Such a device, if not perforated, avoids the problem of excess cement flowing into the appliance by shielding the appliance from the cement, which must flow outwardly from the periphery of the pad, not through it. However, the spot welds destroy the mesh structure at the points of attachment of the screen to the pad, thereby decreasing the effectiveness of the adhesive in bonding the mesh to the tooth. Because of the flexible nature of the screen, many spot welds are necessary to ensure rigidity of this type composite pad, so that the mesh is not very effective. Alternatively, if only a few spot welds are utilized, the mesh flexes so that the effectiveness of the appliance in the orthodontic treatment diminishes.

SUMMARY OF THE INVENTION

According to the present invention, an orthodontic appliance is attached to a tooth by means of a base having a composite cross-sectional configuration with a porous or mesh-like tooth-abutting face which permits the tooth bonding adhesive to enter into but not pass through the base. In one embodiment, the base is a unitary structure, with the porous face formed by casting, chemical etching, or similar processes which will provide cavities, recesses, woven interstitial spaces or the like in the tooth-abutting face, hereinafter generally referred to as being "porous". When in use, an orthodontic appliance extends outwardly from the base opposite the porous face. The appliance may be separately attached to the base by welding, brazing, soldering or the like, or the base and appliance may be a single integral part, in which case, the base, including the porous face and appliance preferably are cast simultaneously by the porous face portion being fixed to or formed in the remainder of the base during the casting operation. In another embodiment, a composite base for direct attachment of an orthodontic appliance to a tooth is formed by a separate mesh portion which is bonded to a metal base portion at each interface between the mesh and the base. In the preferred such embodiment, prior to bonding, pressure is applied to the mesh, either in or out of contact with the base material, to provide a greater area of contact or interface between the mesh and the base during the bonding process by forming flats on the surfaces of the mesh which interface with the base. While various known processes can be utilized to produce the bond, such as diffusion bonding and brazing, a diffusion bonding process is preferably used, during which the temperature is kept below the flow temperature of the base and mesh materials, so that only the "flatted" surface of the mesh material in direct contact with the metal base is bonded. Thus, the base material does not flow into the interstices of the mesh, while a continuous bond is achieved by bonding each interface to the base.

Bases or pads, to which orthodontic appliances are to be attached according to the invention in one of its aspects, preferably are formed from strips of the bonded mesh and metal foil base material by stamping or otherwise forming separate composite pads, preferably to conform to particular tooth surfaces. The porous tooth-abutting mesh surface of the pad is adapted to attach the appliance carrying pad to the surface of a tooth by use of an adhesive. The particular orthodontic appliance is attached to the nonporous surface of the composite pad either by the orthodontist during treatment or during the manufacturing or other processing of the pad. After preparing the surface of the tooth for direct bonding in any well-known manner, the orthodontist applies appropriate cement to the porous face, which is then fixed directly to the tooth. Edgewise brackets, light wire brackets, or any other type of orthodontic device used in the art, may be attached directly to a tooth by utilizing the present invention in any of its many various embodiments.

BRIEF DESCRIPTION OF THE DRAWINGS

The invention may more readily be understood by referring to the accompanying drawings, in which:

FIG. 10 is an isometric view of a portion of mesh for use in one general embodiment of the invention;

FIG. 11 is a partial sectional view of a base and mesh portion of a composite pad according to a particular embodiment of the invention;

FIG. 12 is a partial sectional view of a base and mesh portion according to another particular embodiment of the invention;

FIG. 13 is a view of a strip of composite pads formed by bonding the base strip and mesh strip together and forming individual connected pads having predetermined contours to compliment preselected tooth surfaces, showing the surface of the composite strip to which an orthodontic appliance is attached;

FIG. 14 is a view taken along lines 14—14 of FIG. 10 and illustrating the mesh undersurface of the composite strip for adhesion to the tooth surfaces;

FIG. 15 is a view illustrating a base strip and a mesh strip for use in the preferred embodiment of the invention;

FIG. 16 is a diagrammatic view of the base and mesh strips of FIG. 15 during the step of applying pressure thereto to assist in the bonding process;

DESCRIPTION OF THE PREFERRED EMBODIMENTS

Figure 1:
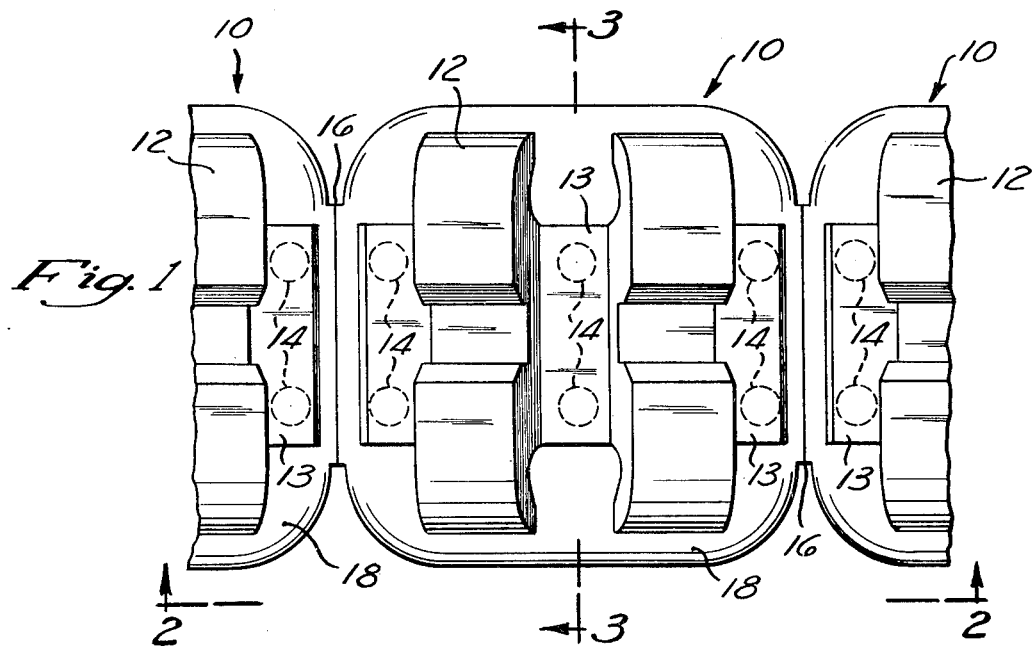
FIG. 1 illustrates a portion of a strip of composite bases or pads constructed in accordance with the invention.

Referring now to FIG. 1, there is shown a view of a portion of a strip of composite pad assemblies 10 constructed in accordance with the present invention. Each of the assemblies 10 has an orthodontic bracket 12, of conventional construction, attached thereto. As shown in FIG. 1, the attachment of the bracket 12 to the pad 10 is at the base portion 13 by means of a series of spot welds 14, shown in dotted lines in FIG. 1. The pads 10 are generally rectangular in shape, with rounded corners, and are connected together at the edges thereof by creased portions 16, so as to permit the facile separation of one pad from the next.

Figure 2:
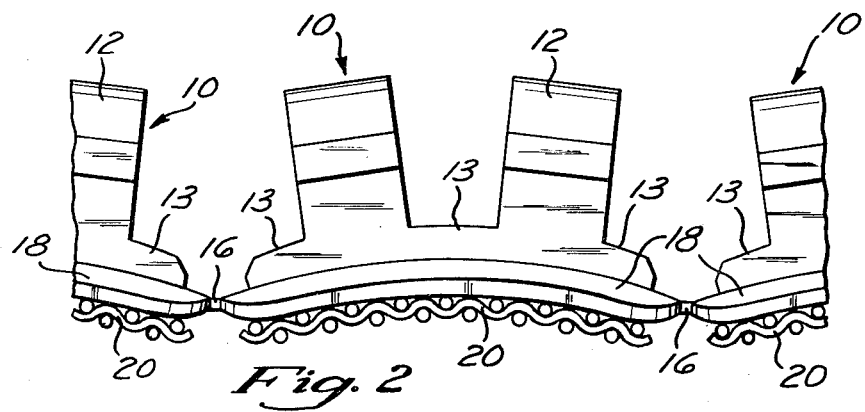
FIG. 2 is a side elevation of the pads of FIG. 1 taken along lines 2—2 of FIG. 1.

Referring now to FIG. 2, there is shown a view, taken along lines 2—2 of FIG. 1, more clearly illustrating the construction of the composite pad strip. In FIG. 2, the composite pads 10 are seen to consist of an upper nonporous surface 18 and a lower porous tooth-abutting surface 20. In the embodiment shown in FIGS. 1-3, the lower porous tooth-abutting surface 20 is a mesh or screen, such as 100 mesh stainless steel terminating in the upper surface 18, which is preferably of a fairly rigid foil, for example stainless steel of about 0.007 inch thickness. The upper and lower surfaces 18, 20 are bonded together at the interfaces therebetween, that is, the individual points of contact of the mesh or screen 20 with the upper surface 18 (see FIGS. 11,12). Such bonding may be by sintering or diffusion bonding, brazing, or the like, as is described hereafter. The pad 10 is seen to be shaped, upon completion of manufacture, so as to generally conform to the surface configuration of a particular tooth. Various pads will have various curvatures to correspond to the different curvatures of the different teeth which may be subject to orthodontic treatment.

Figure 3:
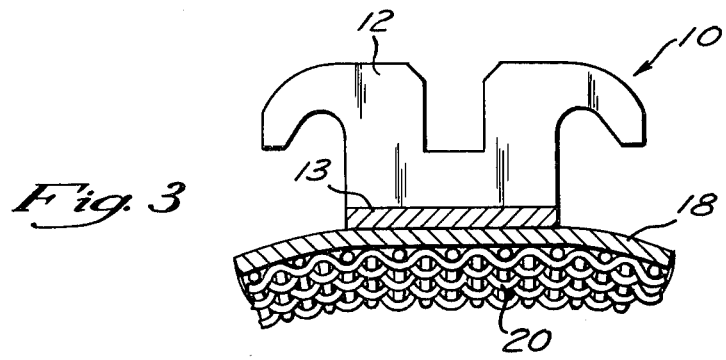
FIG. 3 is a view, in section, taken along lines 3—3 of FIG. 1.

In FIG. 3, there is shown a view, in section, taken along lines 3—3 of FIG. 1, which illustrates the curvature of the pad 10 and the relative disposition of the foil or impervious surface 18 and the porous mesh or screen surface 20.

Figure 4:
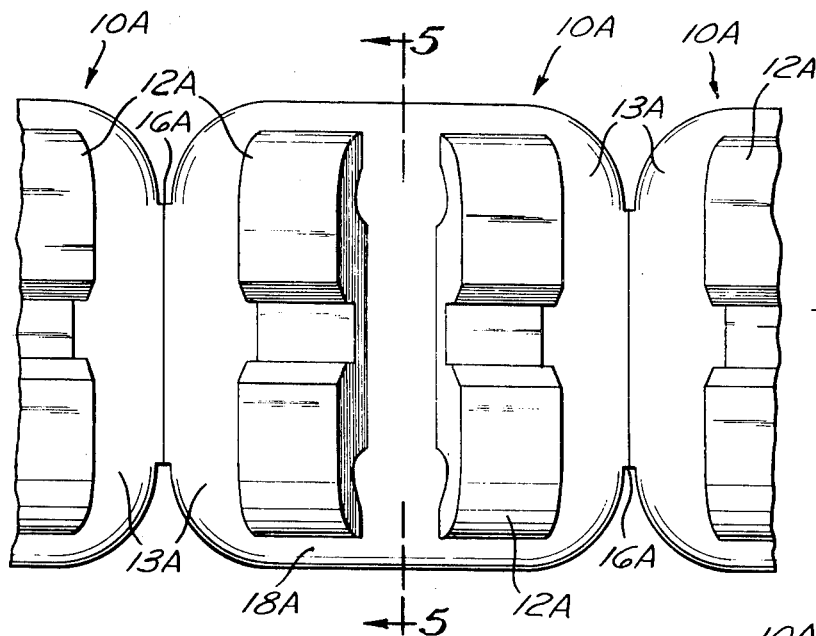
FIG. 4 illustrates a strip of composite pads according to an alternate embodiment of the invention.

FIG. 4 illustrates an alternate embodiment of the invention, being a view of a series of pad assemblies 10A. Each pad assembly 10A has a bracket 12A which has a base portion 13A considerably larger than the base portion 13 of the bracket 12 of FIGS. 1-3. Alternatively, the bracket 12A could be, if desired, a pair of individual brackets, such as is shown in U.S. Pat. No. 3,932,940, the brackets being directly attached to a foil surface corresponding to the foil surface 18 of the embodiment of FIGS. 1-3. In FIG. 4, a series of pads 10A are connected together at their edges 16A in the same manner as those shown with respect to FIGS. 1-3.

Figure 5:
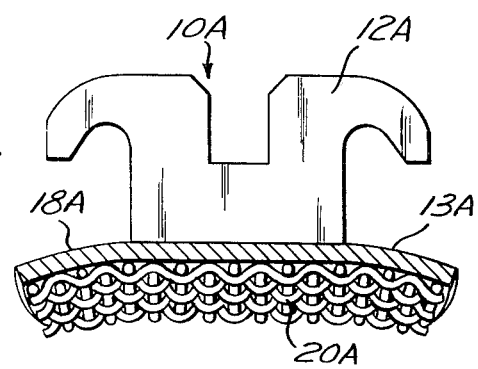
FIG. 5 is a view, in section, taken along lines 5—5 of FIG. 4.

FIG. 5 is a sectional view taken along lines 5—5 of FIG. 4 illustrating the same attachment of mesh surface 20A to the foil or base surface 18A, corresponding to the surface 18 of FIGS. 1-3.

Figure 6:
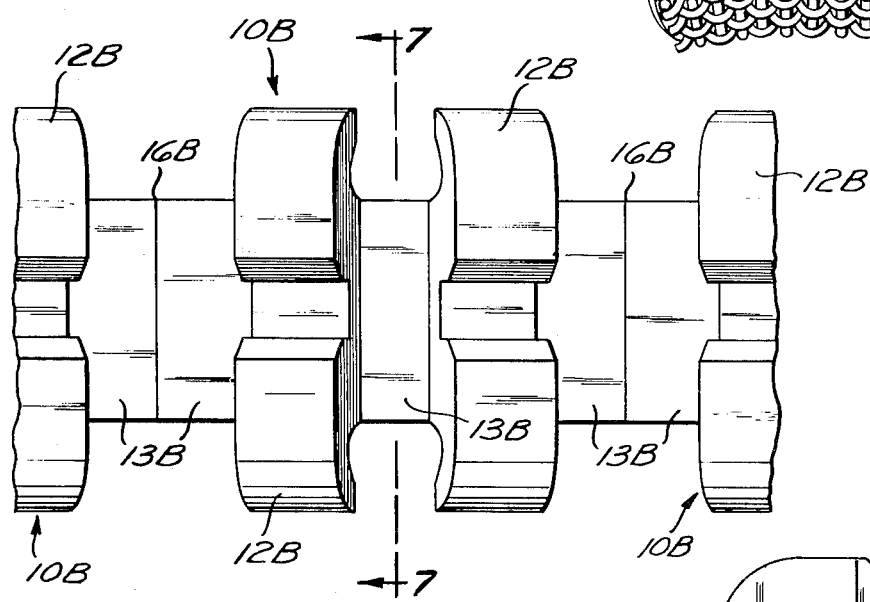
FIG. 6 is a view of another alternate embodiment of a strip of composite pads according to the invention.
Figure 7:
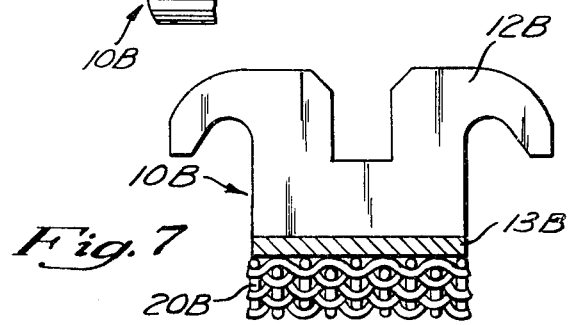
FIG. 7 is a view, in section, taken along lines 7—7 of FIG. 6.

Referring now to FIG. 6, there is shown another alternate embodiment of the present invention in which a composite pads 10B are formed by series of brackets 12B constructed so as to be connected together at the edges of the base portions 13B thereof so as to form creases 16B which permit the facile separation of the adjacent brackets. Attached directly to the base portions 13B by bonding are mesh surface 20B, as is shown in FIG. 7. However, in the embodiment of FIGS. 6 and 7, the shielding effect provided by the wider foil or base portion 18, 18A of FIGS. 1–5 is not present, so that the device of FIGS. 6 and 7 while not permitting the adhesive to pass through the base as is done in U.S. Pat. No. 3,932,940, for example, suffers from the disadvantage of permitting the adhesive, if an excessive amount is used during the process of attachment, to contact the bracket 12B directly, thereby necessitating its subsequent removal by the orthodontist, with the attendant difficulties heretofore described.

Figure 8:
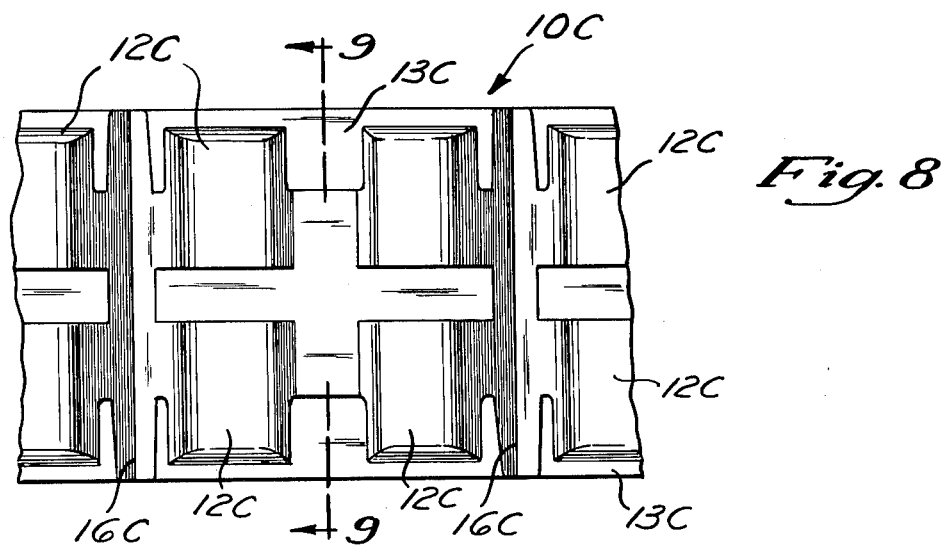
FIG. 8 illustrates a strip of composite pads according to another alternate embodiment of the invention.
Figure 9:
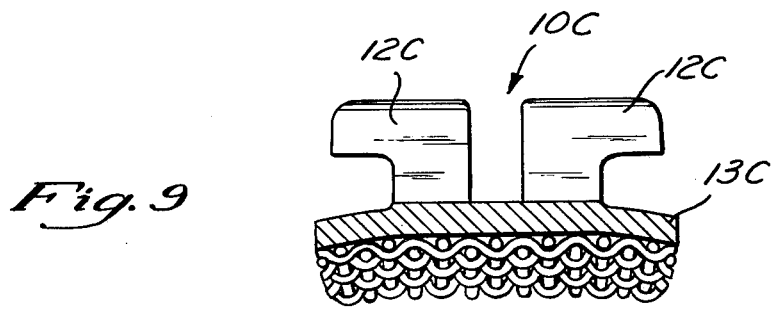
FIG. 9 is a view, in section, taken along lines 9—9 of FIG. 8.

Referring now to FIG. 8, there is shown another alternate embodiment of the present invention in which a strip of brackets 10C have body portions 12C which are integral with base portions 13C. The base portions 13C are connected together at creases 16C. The brackets 10C, as is shown in FIG. 9, have porous tooth-abutting mesh surfaces 20C of the same type as are utilized in the previous embodiments. In the embodiment of FIGS. 8 and 9, the base portions 13C, including the body portion 12C, may be formed by any conventional process prior to bonding the mesh portion 20C thereto. Alternatively, the mesh may be bonded to the base portion prior to forming, by stamping, machining, extruding, or the like of the bracket portion 12C on the base portion 13C. In either event, the base portion 13C terminates in a porous tooth-abutting surface 20C, opposite which the base portion 13C is adapted to have an orthodontic appliance extend outwardly therefrom.

Referring now to FIG. 10, there is shown a portion of mesh 24 for use according to the preferred embodiment of the invention. As will be seen in FIG. 10, the mesh 24 consists of individual mesh elements 28 in a lattice arrangement, onto which flats 30 have been formed in order to provide a greater interface surface area between the mesh and the base portion of the composite base to be formed. The process of forming these flats will be described hereinafter with respect to FIGS. 11 through 16.

Referring to FIGS. 13 and 14, there is shown a strip f partially formed composite pads 10D, each consisting of the metal foil pad 18 which is uniformly secured to the metal mesh pad 20 by bonding at each interface between the mesh and the foil, preferably by the process known as sintering or diffusion bonding. Each composite pad 10D preferably is contoured both laterally and longitudinally as shown in FIGS. 2 and 3 to fit the tooth's curved surface. The foil pad 18 provides a smooth top surface for the composite pad which is suitable for attachment of many different types of orthodontic appliances by spot welding, brazing, or the like. The mesh pad 20 provides a surface suitable for use with appropriate cement, such as a carboxylate cement, for direct bonding of the composite pad to the surface of a tooth.

To produce the composite pads 10D shown in FIGS. 10 and 11, a strip of metal foil 22, as shown in FIG. 15, and a strip of metal mesh material 24 are used. Preferably, in order to assure satisfactory bonding between the mesh strip 24 and the foil strip 22 by increasing the total area of the interface between the foil and individual members 28 of the mesh (see FIG. 11), the mesh strip 24, either alone or with the foil strip 22, is passed through a press, which may consist of a series of rollers (not shown), to provide flats 30 on the circular cross-section of the individual members 28 of the mesh at individual interfaces 32 (see FIG. 11) between the foil 22 and mesh 24. The foil strip 22 and mesh strip 24 are then heat treated in a controlled atmosphere to a temperature which produces sintering bonds 34 between the mesh strip 24 and the foil strip 22 at the interfaces 32 between the mesh members 28 and the foil 22 as well as between the individual mesh members 28, the process being known commercially as diffusion bonding. Pressure is applied to the foil strip 22 and mesh strip 24 as shown in FIG. 16 during the sintering process to assist in the bonding, if desired. In certain applications, this pressure is sufficient to form flats on the mesh, thus eliminating the prior rolling step if otherwise used.

The process of sintering produces a bond between the two metallic strips 22, 24 without actually having any substantial liquid flow between the metals, in order to keep all interstices 36 of the mesh pad 20 substantially free of any such material, thereby retaining the mesh structure intact for adhesive bonding purposes. The sintering produces a bond 34 between the mesh and the foil as illustrated in FIG. 11. In FIG. 11 the foil 22 is fixed to the mesh 24 at the interface flats 30 on the individual strands 28 of the mesh to provide a mesh to foil bond 34 of great strength, while mesh strand to mesh strand bonding 34A increases the rigidity of the composite pad over a composite pad with only a mesh to foil bond.

Both the foil strip 22 and the mesh strip 24 are preferably stainless steel. The foil may typically be of 0.007 inch thickness. The mesh is preferably 100 squares per inch, with a wire diameter of about 0.0045 inches, although other meshes may be suitable in order to obtain complete bonding of all the mesh pads to be produced from the foil-mesh strip. The rolling and pressing may be repeated successively several times, if required, to provide the proper surface area of the flats on the mesh strip 24 for diffusion bonding.

The composite pads preferably are not formed individually, but rather in a multiple strip by cutting, stamping or some other suitable operation on the flat foil-mesh strip after bonding to provide the strip 10D as shown in FIGS. 13 and 14. For purposes of handling, the strips of composite pads can be simultaneously formed with the individual pad joined at the edges as indicated at 16. These strips of pads are now suitable for handling for attachment of various orthodontic appliances. Alternatively, individual separate pads can be provided in various assortments of sizes and contours to provide for the differences in sizes and shapes of the various teeth.

In FIG. 12, there is shown an alternate embodiment of bonding, in which the individual strands 28 of the metal are not flattened. The bonding is shown at 34B, as brazing or the like, although sintering or diffusion bonding may also be used, just as brazing may be used in the embodiments of FIG. 11. As will be seen, the individual interface surface areas between the mesh and the foil are much less than in the preferred embodiment of FIG. 11. Such bonding may be accomplished by plating either the foil 22 or the mesh 24, or both, with a very thin coating of a suitable material, such as gold or nickel, before sintering. A very thin fillet of braze material results at each point of contact between the foil and mesh during the heating of the two metals. This method can be practical and economical as the braze will flow in a controlled atmosphere without flux. The brazing may be accompanied by sintering, if desired.

Brazing may also be provided by sandwiching a very thin sheet of brazing material, such as a nickel alloy, between the foil 22 and the mesh 24 and then sintering in a controlled atmospheric furnace. Care must be exercised to avoid an excess of brazing material between the foil 22 and the mesh 24, which, otherwise, will fill the interstices 36 between the mesh and the foil, thereby reducing the adhesion capability of the composite pad to the tooth.

The composite pads 10, 10A, 10B, 10C, 10D, having metal bases, preferably sintered or diffusion bonded to the mesh, provide superior orthodontic apparatus for direct bonding of appliances to the teeth. To apply the appliance to the tooth, the tooth is first etched with a suitable etching compound such as phosphoric acid and then an adhesive is smoothed onto the etched tooth enamel. The pad carrying the orthodontic appliance is then pressed onto the bonding material, causing the bonding material to flow into the interstices 36 of the porous tooth-abutting face, around the individual strands 28 to create a bond to the tooth which is many times the bond strength of previous pads when bonded directly to a tooth. While FIGS. 1-9 illustrate attachment of an edgewise bracket, the composite pad may be used with other devices, such as light wire brackets, buccal tubes, hooks, and the like to provide the strongest possible uniform bond of orthodontic appliance to the tooth by direct bonding.

The particular temperature and atmosphere used during the sintering or diffusion bonding process depends, of course, upon the particular materials selected for producing the mesh strip and base bond. As the sintering process consists of heating the materials to be bonded to a temperature below the flow temperature, it is imperative that the characteristics of the particular materials being used should be known. In the process of sintering two materials, there is a temperature at which the materials become somewhat fluid, but it is preferred that in the practice of the present invention that such temperatures not be reached, thereby avoiding any substantial flow of material.

In the sintering process, the mesh portion of the composite pad is fixed to the base portion, thereby greatly increasing the rigidity of the composite pad over the base portion alone, particularly in the embodiment of FIGS. 1-3, in which a foil base is used. The rigidity of the composite pad is also increased by the individual members of the mesh portion becoming sintered to one another at the points of contact between cross-members. Thus, the mesh portion alone, after sintering, is much more rigid than prior to sintering, and the composite pad provides a structure which can be formed, during manufacture, to conform to the various contours of the appropriate portions of different teeth. Once so formed, the composite pad retains the desired contour, even during attachment of the orthodontic appliance, if the appliance has not been attached prior to shaping the pad to the desired tooth conforming contour. By selecting one of a series of shaped pads which is appropriate for the particular tooth to which the appliance is to be fixed, the orthodontist need not himself be concerned with shaping the pad. Thus, by maintaining a supply of various pad sizes and contours, the orthodontist can readily meet the requirements of a particular patient for the entire orthodontic treatment.

The foregoing description of the preferred form of this embodiment of the invention provides for the production of "flats" on the mesh prior to or during bonding. While such an embodiment is preferred, the mesh can be satisfactorily bonded to the base without the utilization of flats, provided that bonds at substantially all of the individual interfaces between the mesh and the base are achieved. Also, while the attachment of the orthodontic appliance to the base is described heretofore as occurring after the bonding of the mesh to the base, the appliance can be attached to the base in serial fashion prior to bonding, if desired. Such a variation in the method of the present invention produces a pad which avoids the damage to part of the mesh surface which may otherwise occur during the subsequent attachment of the appliance to the pad, particularly if spot welding is used.

While, embodiment described utilizes stainless steel, other metals can be used if desired. Also, non-metallic meshes can be used, provided that a satisfactory bonding process is available to bond the mesh to the base. In its broadest sense, the pad of the present invention has a base with a porous tooth-abutting face which terminates in a non-porous portion. However the formation of the porous surface is not limited to the utilization of meshes. For example, small stainless steel spheres, about 0.006 inches in diameter, can be used in place of the mesh and one or more layers bonded directly to each other and the base to provide the porous surface for attachment of the composite pad to the tooth. The term mesh, therefore, contemplates porous tooth-abutting surface portions with interconnected interstitial passages generally, and is not necessarily limited to the use of screen type meshes unless specifically so defined in the claims hereof.

Figure 17:
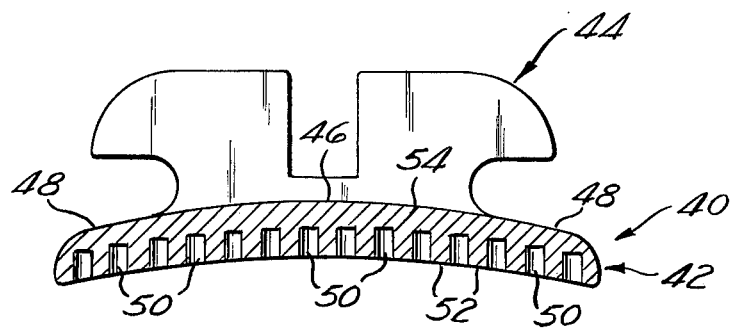
FIG. 17 is a cross-sectional view of an alternate embodiment of orthodontic appliance according to the present invention adapted to be cast as a unitary structure.

Referring now to FIG. 17, there is shown, in cross-section, an orthodontic device 40 including a base 42 and a bracket portion 44. The base 42 is shown in section and has a central portion 46 and a pair of shoulders 48. Thus, the orthodontic device 40 shown in FIG. 17 corresponds generally to the device 10 shown in FIGS. 4 and 5 in overall dimensions. Alternatively, the orthodontic device 40 can have a narrower base portion, such as is generally shown with respect to the orthodontic appliance 10B of FIGS. 6 and 7. As seen in FIG. 17, the base 42 has a series of pore-like cavities or recesses 50 forming a tooth-abutting surface 52 thereof. The tooth abutting surface 52 is porous and terminates in an upper base portion 54 which is non-porous and which is adapted to have the actual orthodontic appliance in this case, the bracket portion 44, extend outwardly therefrom. The device 40 may be formed by casting, with the porous surface 52 formed at the time of casting of the bracket portion 40 casting or, alternatively, the porous surface 52 may be formed subsequent to forming the base portion 42, by chemical etching, drilling, or any other comparable method. Thus, the appliance 40 of FIG. 17 has a porous toothabutting surface with interstitial spaces adapted to receive an adhesive to permit the adhesive to pass into, but not through, the base 42. The adhesive bonds the base 42 and thus the appliance 40 to the tooth.

Figure 18:
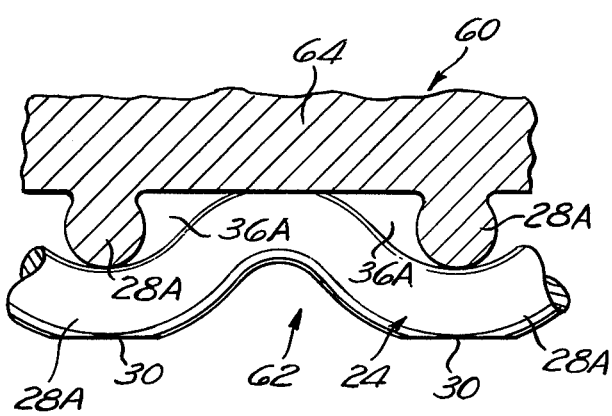
FIG. 18 is a partial cross-sectional view of another embodiment of a cast orthodontic appliance according to the present invention.

FIG. 18 illustrates a partial sectional view of an alternate embodiment of a cast unitary structure orthodontic appliance of the general type described with respect to FIG. 17. However, the device of FIG. 18 has a base portion 60 with a porous face 62 having a mesh-like or woven appearance generally similar to that shown with respect to the devices of FIGS. 1 through 16. Thus, the base portion 60, in addition to the porous tooth-abutting face 62, has a non-porous portion 64 from which the porous face 62 extends outwardly for contact with the tooth. However, the porous face 62 has individual members 28A, generally similar to the members 28 of FIGS. 11, 12, but formed differently. The appliance of FIG. 18 is formed by the "lost wax" method of casting, in which a model of the appliance is made of wax or similar material. A mold is then formed about the wax model and the wax removed by heating or a similar process. This method produces a mold cavity which conforms to the precise configuration of the appliance to be formed. Hollow portions conform to the individual crossing members 28A which are to form the porous surface 62. By having mold material conforming to interstices 36A in the appliance of FIG. 18. The mold cavity is then filled with molten metal which is to form the appliance, and after solidification, the mold material is removed from around the appliance. Mechanical means such as sand blasting or chemical means such as dipping in a caustic solution, or combinations of mechanical and chemical means may be utilized for this purpose.

Figure 19:
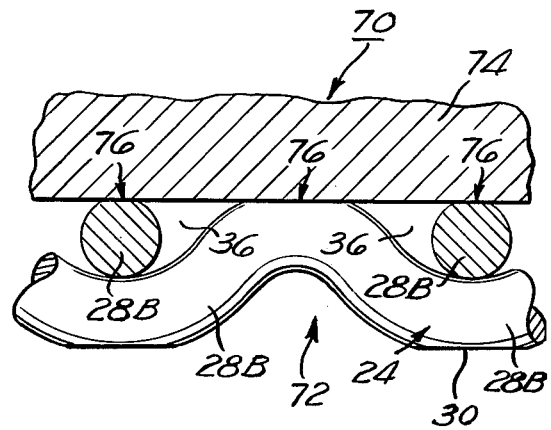
FIG. 19 is a partial cross-sectional view of a further alternate embodiment of cast orthodontic appliance according to the present invention.

FIG. 19 illustrates the base portion 70 of an alternate embodiment of cast orthodontic appliance according to the present invention, having a porous surface 72 formed differently from that described with respect to FIG. 18. The porous surface 72 consists of individual crossing members 28B which are formed of a screen or mesh generally similar to that described in FIGS. 1 through 16. The appliance 70 has a non-porous cast portion 74. The members 28B are in the mold at the time of casting. The casting process results in some melting of the members 28B in the mold between the points of contact 76 between members 28 and the molten material which is to form the solid base portion 74. When the casting has cooled, the appliance shown in FIG. 19 is removed from the mold as described above with the members 28 thereby fixed to the base portion 74, thereby providing a unitary structure having a porous tooth-abutting surface 72 terminating in a non-porous portion 74 which is adapted to have an orthodontic appliance extend outwardly therefrom away from the tooth-abutting surface 72. Interstices 36 in the porous surface 72 permit adhesive utilized to attach the appliance shown in FIG. 19 to a tooth to enter into the porous surface 72, while the non-porous portion 74 prevents the adhesive from passing through the base 70.

Figure 20:
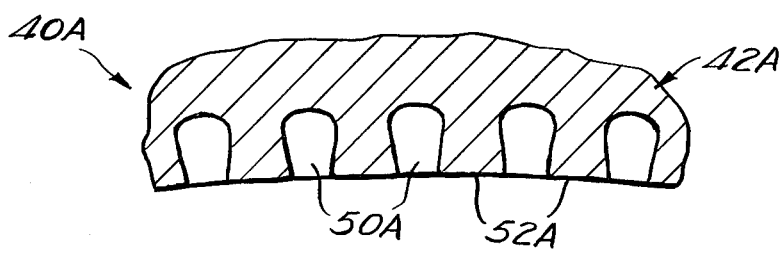
FIG. 20 is a fragmentary cross-sectional view of a modification of the embodiment of FIG. 17.

FIG. 20 shows a fragmentary cross-sectional view of a modification of the embodiment illustrated in FIG. 17. In FIG. 20, an orthodontic device 40A, which is generally the same as the device 40 of FIG. 17, has a base 42A, into which a series of pore-like cavities or recesses 50A extend to form a tooth-abutting surface 52A. The cavities 50A differ from the cavities 50 of the device 40 of FIG. 17 in being slightly undercut as the cavities 50A extend away from the tooth-abutting surface 52A, thus forming bulb-like recesses. These bulb-like recesses provide, in conjunction with the adhesive used to attach the device 40A to the tooth, a greater holding power than exists with the generally cylindrical recesses 50 of the embodiment of FIG. 17 which do not have the undercut configuration. While the device 40A can be formed either by casting or chemically etching the recesses 50A in the base 42A, a chemical etching process is preferred.

The foregoing description of the preferred embodiments are given by way of description only, and are not intended to limit the scope of the invention except in accordance with the claims hereof.

The invention claimed is:

1. Apparatus for use in the practice of orthodontics by being fixed to a tooth by means of an adhesive comprising:
   a base having
   a. a first portion which is a mesh with cross-members which are bonded together at each point of intersection therebetween, said first portion having an outer tooth-contour conforming face and an inner face and
   b. a second non-porous portion co-extensive with the said first portion; said first portion terminating in said second portion at the inner face of the mesh by a bond therebetween opposite each cross-member bond; and
   an orthodontic appliance extending outwardly from the second portion remote from said first portion, whereby said adhesive enters the mesh-like tooth-abutting surface portion but does not pass through the base to reach the orthodontic appliance.

2. The apparatus of claim 1, and in which the the first portion is about 100 mesh.

3. The apparatus of claim 2, and in which the first and second portions are in physical contact with one another, and in which the first portion to the second portion at flats formed on the inner face to facilitate the bond.

4. The apparatus of claim 2, and in which the bond includes a brazing bond.

5. The apparatus of claim 2, and in which the bond includes a diffusion bond.

6. An orthodontic apparatus for direct bonding comprising:
   a first pad which is non-porous and adapted to have the orthodontic appliance fixed thereto;
   a second pad which is of mesh configuration and is co-extensive with and abutting the first pad for receiving an adhesive for attaching the composite pad to a tooth;
   means for bonding the first pad to the second pad at the individual interfaces therebetween so that the mesh forms a series of innerconnected interstitial adhesive receiving passages; and
   an orthodontic appliance extending outwardly from the first pad.

7. The composite pad of claim 6, and in which the first pad is a metal foil.

8. The composite pad of claim 6, and in which the second pad is a metal mesh.

9. The composite pad of claim 7, and in which the second pad is a metal mesh.

10. The composite pad of claim 9, and in which the bonding means includes a diffusion bond.

11. The composite pad of claim 9, and in which the first pad is of about 0.007 inch thickness and the second pad is about 100 mesh whose individual mesh-forming members are of about 0.0045 inch in diameter.

12. The composite pad of claim 9, and in which the first and second pads are made of stainless steel.

13. The composite pad of claim 9, and in which the first and second pads are in physical contact with one another, and in which the surface of the second pad in contact with the first pad has flats formed thereon to facilitate the bond.

14. The composite pad of claim 9, and in which the bonding means includes a brazing bond.

15. The composite pad of claim 13, and in which the bonding means includes a diffusion bond.

16. An orthodontic apparatus comprising:
   a composite base pad having a first base pad portion of a metal foil and a second base pad portion of a metal mesh, said first and second pad portions being coextensive with and abutting one another and forming the composite pad by being bonded together at the individual interfaces between the mesh and foil;
   an orthodontic appliance; and
   means for fixing the orthodontic appliance to the foil surface portion of the composite pad.

* * * * *

UNITED STATES PATENT OFFICE
CERTIFICATE OF CORRECTION

Patent No. 4,068,379　　　　　Dated January 17, 1978

Inventor(s) Frank R. Miller, et al.

It is certified that error appears in the above-identified patent and that said Letters Patent are hereby corrected as shown below:

Col. 10, line 13　　after "which the" delete --the--

Col. 10, line 17　　after "first portion" insert --is bonded--

Signed and Sealed this

Twentieth Day of June 1978

[SEAL]

Attest:

RUTH C. MASON
Attesting Officer

DONALD W. BANNER
Commissioner of Patents and Trademarks